United States Patent [19]

Pequignot

[11] Patent Number: 5,171,282
[45] Date of Patent: Dec. 15, 1992

[54] FEMORAL MEMBER FOR KNEE PROSTHESIS

[75] Inventor: Michel Pequignot, Clamart, France

[73] Assignee: Societe Civile d'Innovations Technologique, Noisy sur Ecole, France

[21] Appl. No.: 637,626

[22] Filed: Jan. 4, 1991

[30] Foreign Application Priority Data

Jan. 12, 1990 [FR] France .................. 90 00335

[51] Int. Cl.⁵ ........................................... 623 18
[52] U.S. Cl. ........................................... 623/20
[58] Field of Search ........................ A61F/2/38

[56] References Cited

U.S. PATENT DOCUMENTS

| | | | |
|---|---|---|---|
| 3,715,763 | 2/1973 | Link | 128/92 |
| 4,000,525 | 1/1977 | Klawitter | 128/92 |
| 4,865,607 | 9/1989 | Witzel et al. | 623/20 |
| 4,911,721 | 3/1990 | Bränemark et al. | 623/20 |
| 5,021,061 | 6/1991 | Wevers et al. | 623/20 |
| 5,080,674 | 1/1992 | Jacobs et al. | 623/20 |

FOREIGN PATENT DOCUMENTS

| | | | |
|---|---|---|---|
| 449173 | 4/1968 | Switzerland | 623/22 |
| 1527498 | 10/1978 | United Kingdom | 623/22 |

Primary Examiner—David Isabella
Attorney, Agent, or Firm—Longacre & White

[57] ABSTRACT

The femoral part (15) is, for example, of the kind comprising two lateral branches (16) each adapted to be applied to a respective condyl of the femur to be treated, to cooperate with the glenes of the corresponding tibial plates, and a median part (20) to which the aforementioned lateral branches (16) are joined.

According to the invention, at least part of the rubbing surface of the femoral part (15) is provided with a ceramic facing (22); for example, this applies to each of its lateral branches (16) over part at least of their length.

Application to full knee prostheses.

9 Claims, 2 Drawing Sheets

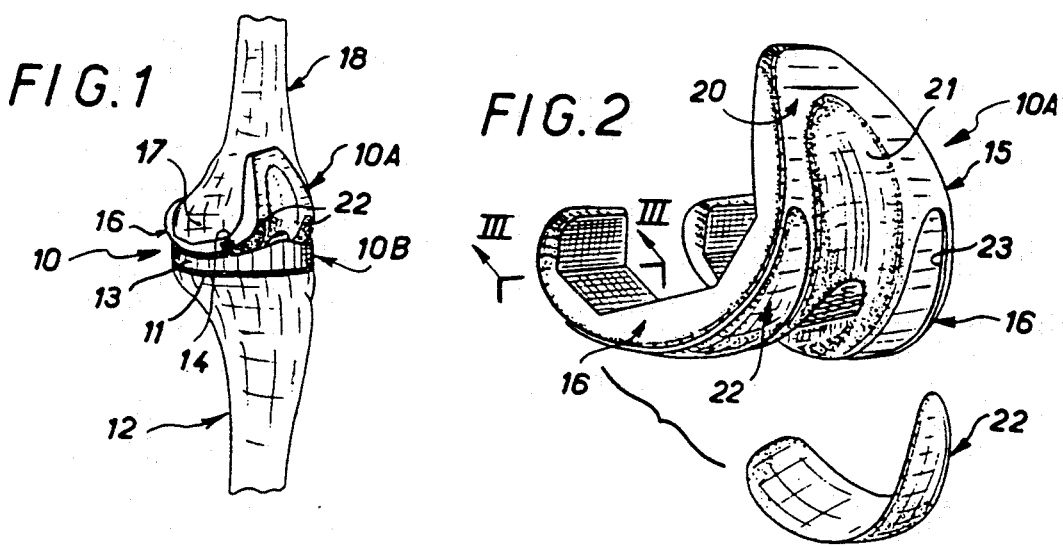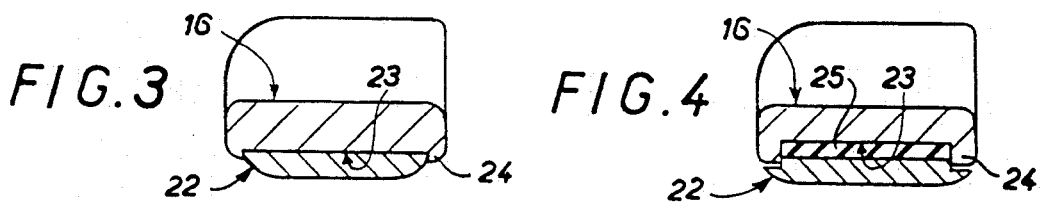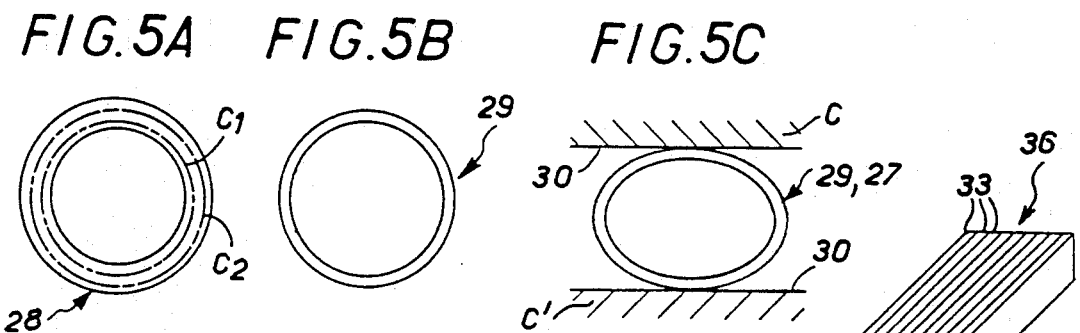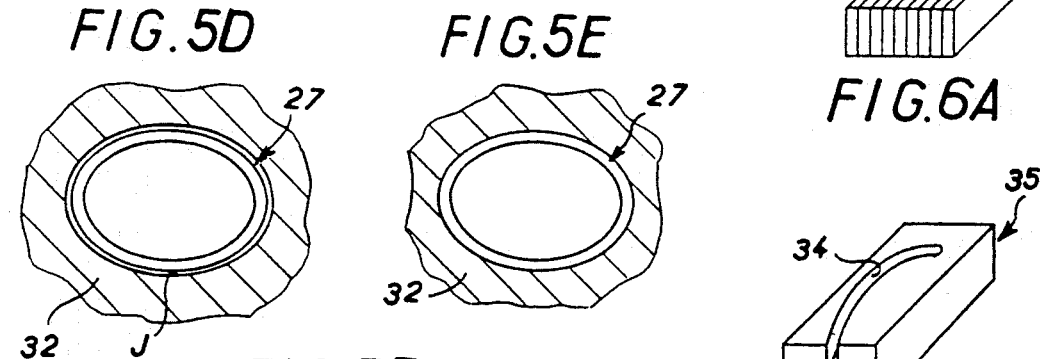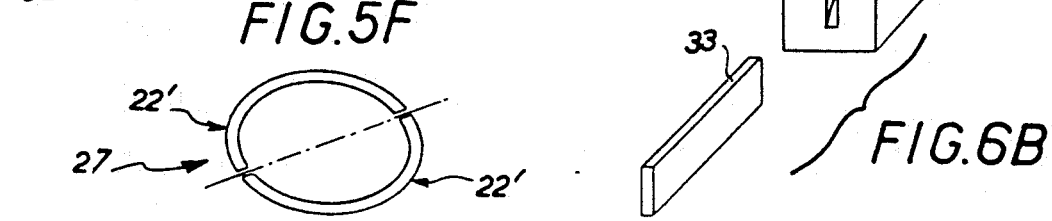

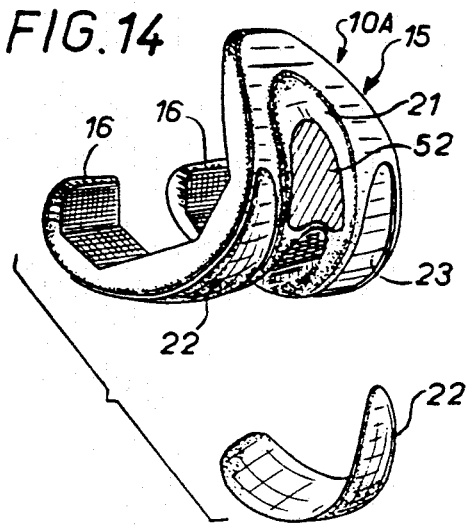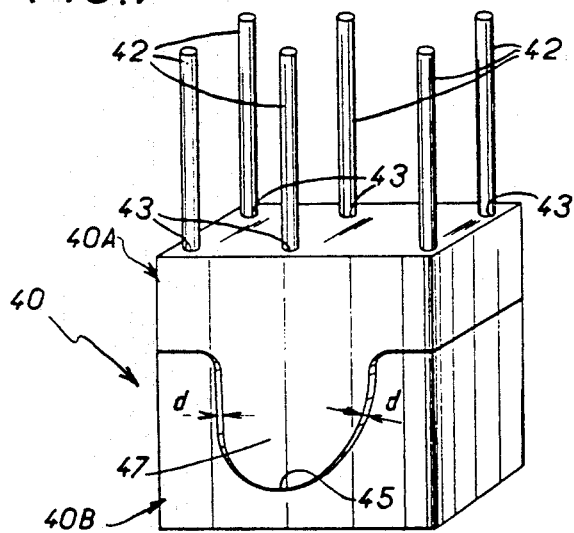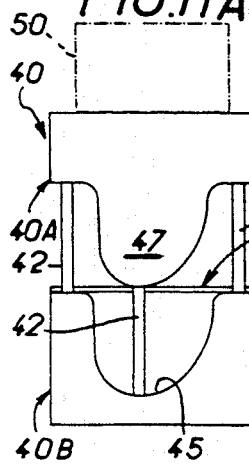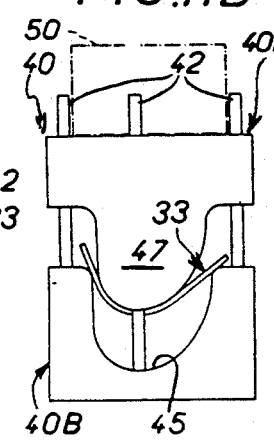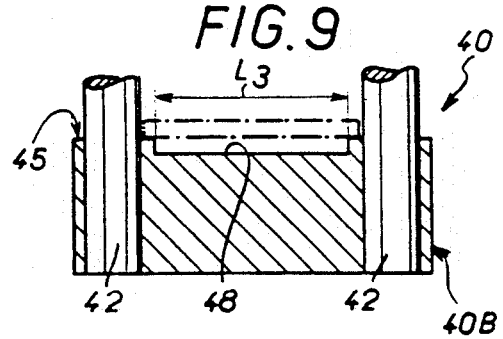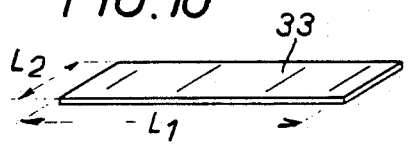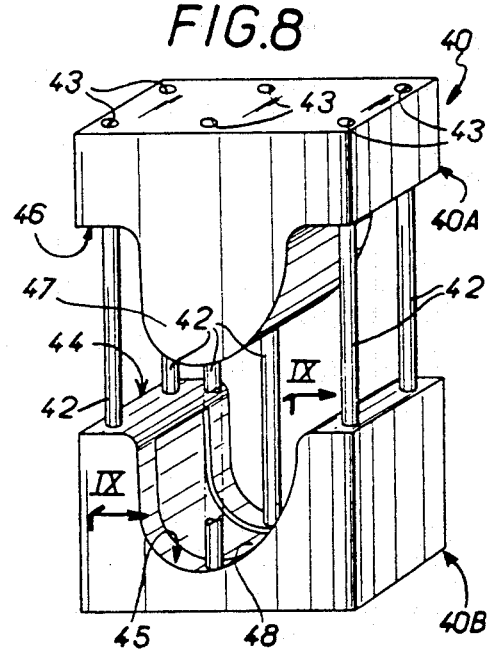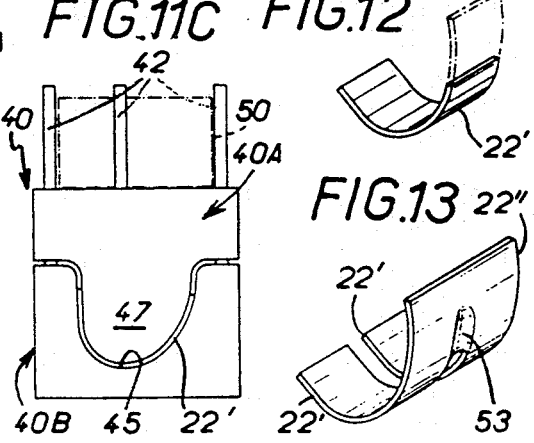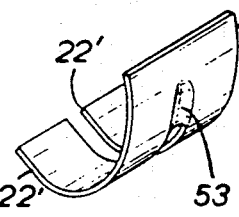

FEMORAL MEMBER FOR KNEE PROSTHESIS

The present invention is generally concerned with full knee prostheses of the type used in the case of very advanced arthrosis.

It is more particularly directed to the femoral parts of such prostheses.

These are, for example, in one piece in the shape of a curved fork having two lateral branches each adapted to be applied to a respective condyl of the femur to be treated, to cooperate with the glenes of the corresponding tibial plate, and a median part to which the two lateral branches are joined and which has at the root of the latter a broadly rounded groove forming the associated femoral trochlea.

This femoral part, whose shape is therefore relatively complex, and which is retained on the femur, after the latter is prepared, essentially by means of a nesting type interengagement must necessarily be extremely rigid.

As described in the French patent application published under the number 2 142 028, this part is always a metal member which is cast, for example, often using the lost wax casting process, from metals and metal alloys selected for their biocompatibility, such as low-carbon stainless steel, chromium-nickel-cobalt alloy, titanium alloy and titanium-vanadium alloy.

One of the problems in manufacturing full knee prostheses incorporating a femoral part of this kind results from the fact that, unlike spheroidal type prostheses in which the rubbing surfaces or contact surface which is adapted to be in engagement with the tibial part of the knee prothesis, are a perfect fit, the articulation to be reproduced requires the corresponding rubbing surfaces to be a rather loose fit, in particular because the flexion-extension movements occurring during normal walking, for example, entail sliding as well as rolling of the condyls on the glenes.

It is therefore important for there to be a good adaptation to rubbing contact between the femoral part of a full knee prosthesis and its tibial part.

To this end the tibial part usually comprises a friction part made from synthetic material, high-density polyethylene in practise, on which the glenes of the tibial plate to be reproduced are formed and which is attached to a metal support part fastened into the tibia.

Unfortunately, the high-density polyethylene which is indispensable for this application tends to become abrasive as it deteriorates.

As a result, and following a cycle which inevitably accelerates, it begins to attack the metal femoral part with which it is in contact, especially if the latter is made from low-carbon stainless steel or titanium alloy.

Surface treatment to confer some degree of surface hardening to the rubbing surfaces of the femoral part, which must be highly polished, has previously been proposed.

In the case of a titanium alloy femoral part, for example, nitriding by ionic implantation has been proposed.

Nitriding is capable of producing highly favorable surface hardness and friction coefficient properties.

However, its use requires very complex techniques and extreme care as to the cleanliness of the surfaces to be treated, which are polluted as a result of previous polishing.

It is therefore particularly costly.

Finally, and most importantly, the thicknesses effectively treated are always very small, in the order of two microns, for example. This results in the formation of a surface layer which is very hard but which is also very fragile and which in particular is liable to become impacted in the underlying, softer metal substrate.

Another proposal is to coat the rubbing surfaces to be treated with metal oxide ceramic by plasma sputtering of the relevant metal oxides.

The resulting deposits are known to be thicker than those previously described, reaching values in the order of a few tenths of a millimeter, for example, and have the advantage of being particularly hard and of having an excellent friction coefficient.

However, they have the three-fold drawback of needing polishing for this friction coefficient to be achieved, of being porous, which renders them liable to trap unwanted particles and in particular those resulting from previous polishing, and of having a limited adhesion to the underlying substrate with the risk that they may be partly detached from the substrate leading to fast and irreversible deterioration of the rubbing surfaces.

It is not economically feasible to make the femoral part in one piece from ceramic, because of the cost of the metal oxide used, the shrinkage of the ceramic that occurs on firing and the cost of subsequent machining of the ceramic.

A general object of the present invention is an arrangement which overcomes these problems to enable the use of ceramic for a femoral part for a full knee prosthesis.

To be more precise, its first object is a femoral part for a knee prosthesis characterized in that at least part of its rubbing surface is provided with a ceramic facing or solid ceramic liner strip.

The facing is attached like a rim to the femoral part to which it is appropriately attached, as by crimping or adhesive bonding, for example, and is therefore distinguished from a directly deposited surface coating, which advantageously makes it possible to minimize the quantity of ceramic used by restricting it to that part only of the femoral member which is actually subject to friction.

However, being made from solid ceramic, it does not have the disadvantages of this type of surface coating as explained above.

If, in the usual way, the femoral part is of the kind in the general shape of a curved fork, with two lateral branches each adapted to be applied to a respective condyl of the femur, to cooperate with the glenes of the corresponding tibial plate, and a median part to which said two lateral branches are joined, each of its lateral branches is provided over at least part of its length with a ceramic facing.

There remains the problem of manufacturing the ceramic facing, its shape being relatively complicated and normally requiring precise adjustment.

Other objects of the present invention are various methods for manufacturing a ceramic facing of this kind at acceptable cost, without requiring costly machining.

A first of these methods entails cutting a flattened ceramic ring diagonally.

The flattened ring may be obtained by heating and flattening under load an initially cylindrical ring, for example, after which it is placed in a mold made from a material whose coefficient of thermal expansion is less than its own, exploiting the difference between the two coefficients of thermal expansion.

Be this as it may, a method of this kind has the advantage of forming simultaneously two facing blanks which are then machined to polish and taper them and which are adapted to be fitted conjointly to the same femoral part.

A second method in accordance with the invention entails forming the facing blanks individually by heating a ceramic plate and forcing it into a groove shaped to the required profile.

A third method entails forming a facing blank by inserting a ceramic plate between two parts of a mold which are then moved together at raised temperature.

In either case, the resulting facing blank is then machined.

In practise, these various methods have as their common feature the conforming of a pre-existing ceramic part to enable its application to the femoral member.

A final object of the invention is a method for manufacturing the femoral part of a knee prosthesis characterized in that it entails forming as a separate part at least on ceramic facing and attaching said ceramic facing to a metal femoral part or support member, itself adapted to be attached to the femur.

The objects of the invention, their characteristics and their advantages will emerge from the following description given by way of example with reference to the appended diagrammatic drawings in which:

FIG. 1 is a perspective view of a knee prosthesis using a femoral part in accordance with the invention;

FIG. 2 is a perspective view to a larger scale of the femoral part alone with one of its two ceramic facings in place and the other separated from it;

FIG. 3 is a partial view of the femoral part in transverse cross-section on the line III—III in FIG. 2;

FIG. 4 is a partial view in transverse cross-section analogous to that of FIG. 3 showing another embodiment of the femoral part in accordance with the invention;

FIGS. 5A, 5B, 5C, 5D, 5E and 5F are plan or plan-section views showing various successive phases of a method in accordance with the invention for manufacturing a ceramic facing of this kind;

FIGS. 6A and 6B are perspective views showing two successive phases of another method in accordance with the invention for manufacturing a ceramic facing of this kind;

FIG. 7 is a perspective view of a mold used in another method in accordance with the invention to form a ceramic facing of this kind, showing the mold in the closed, empty position;

FIG. 8 is a perspective view analogous to that of FIG. 2 showing the mold in the open position;

FIG. 9 is a partial view of one part of the mold to a larger scale in transverse cross-section on the line IX—IX in FIG. 8;

FIG. 10 is a perspective view to the same scale as FIGS. 7 and 8 of a ceramic plate ready to be shaped;

FIGS. 11A, 11B and 11C are elevation views of the mold in accordance with the invention to a smaller scale, showing various successive phases of its operation;

FIG. 12 is a perspective view of the facing blank produced by this forming operation;

FIG. 13 is a perspective view analogous to that of FIG. 12 showing another embodiment;

FIG. 14 is an exploded perspective view analogous to that of FIG. 2 showing an alternative embodiment.

As shown in FIG. 1, a full knee prosthesis 10 comprises a femoral part 10A and a tibial part 10B.

The invention is concerned only with the femoral part 10A.

With regard to the tibial part 10B, suffice to say that it usually comprises, as shown here, two parts, namely a support part 11 which is usually made of metal and which is fastened into the end of the tibia 12 and a friction part 13 attached to the support part 11 and made from a synthetic material, in practise from high-density polyethylene, forming the tibial plate 14 with the articulation surfaces or glenes (not shown in the figure) on which the femoral part 10A rolls and slides.

In practise the femoral part 10A is reduced to a single femoral part generally indicated in the drawings by numeral 15, which includes a support member 15A.

By virtue of arrangements which are well known in themselves and will not be described here because they do not form any part of the present invention, the support member 15A, which is in practise a metal part, is adapted to be attached to the end of the femur 18, by means of screws, for example.

In the embodiment shown here, its general shape is that of a fork curved around a horizontal axis with two lateral branches 16 each adapted to be applied to a respective condyl 17 of the femur 18 and to cooperate with a respective glene on the tibial plate 14 and a median part 20 to which the lateral branches 16 are joined in a V-shape overall and which comprises, at the root of the lateral branches, a largely rounded groove 21 forming the associated femoral trochlea.

According to the invention, at least part of the rubbing surface of the femoral part 15 is provided with a ceramic facing.

In the embodiment shown in FIG. 2, this is the case for both lateral branches 16.

According to the invention, each of the lateral branches 16 is therefore provided over at least part of its length, and in practise over all of its effective length, with a ceramic facing 22.

The ceramic facings 22 fitted to the support member 15A are solid ceramic members initially separate from the support member 15A and attached to it by suitable means.

In FIGS. 1 to 3, for example, each of the ceramic facings 22 is inserted into a housing 23 provided for this purpose on the corresponding lateral branch 16 and is crimped into the latter by folding over against it the edges 24 of the housing 23.

As an alternative (FIG. 4) it may be attached by adhesive bonding.

In the embodiment shown in FIG. 4, damping means are additionally disposed between a lateral branch 16 of the femoral part 15 and the ceramic facing 22 that it carries.

This is an elastic material pad 25, for example, as shown here.

The pad 25 is inserted into the housing 23, to the bottom of which it is adhesively bonded.

The ceramic facing 22 can then be attached by adhesive bonding.

In the embodiment shown here, the ceramic facing 22 extends beyond the contour of the housing 23 and overlies with clearance its edges 24.

This is not mandatory, however.

Be this as it may, each of the lamellar ceramic facings 22 is curved about an axis at right angles to its longer dimension and narrows asymmetrically from the rear towards the front.

The ceramic facings 22 are tapered on the side of the groove 21 forming the femoral trochlea and are generally symmetrical to each other relative to the axis of the femoral trochlea.

The ceramic facings 22 are preferably made from a metal oxide ceramic with optimal properties of biocompatibility, mechanical strength and coefficient of friction in contact with high-density polyethylene.

Zirconia, and to be more precise zirconia stabilized with 3% yttrium oxide, is entirely satisfactory in this respect, in particular because of its very small grain size which enables a particularly high polish to be achieved.

Alumina with a larger grain size can be equally suitable, however.

Nevertheless, the ceramic facings 22 used in accordance with the invention are preferably made from zirconia.

In the longitudinal direction the shape of the ceramic facings 22 resembles an ice skate, the front part being more raised and more curved than the rear part.

Noting that, when put together head-to-tail, the ceramic facings 22 together form a flat ring, a first method in accordance with the invention for manufacturing the ceramic facings 22 involves cutting diagonally a flattened ceramic ring 27, as shown by the chain-dotted line in FIG. 5F, this first method having the advantage of producing two facing blanks 22' simultaneously.

This method will now be described in more detail.

As schematically represented in FIG. 5A, the initial product is a ceramic ring 28 obtained in the usual way by firing a blank obtained by isostatic pressing.

Because of the shrinkage which occurs during firing, the ceramic ring 28 is not strictly cylindrical.

It is therefore machined internally to form the cylinder C1 shown in chain-dotted outline in FIG. 5A and externally to obtain the cylinder C2 also shown in chain-dotted outline, yielding a perfectly cylindrical ceramic ring 29 (FIG. 5B).

As this ring is made from zirconia, the property of a ceramic of this kind to deform when loaded at high temperature is exploited.

As schematically represented in FIG. 5C, the initially cylindrical ring 29 is flattened by applying a load at high temperature.

To achieve the required flattening it is sufficient, for example, to apply to the initially cylindrical ring 29 a load of 3 kg at a temperature in the order of 1,500° C.

The heat treatment cycle can, for example, entail an increase in temperature at 5° C./min up to 1,000° C. and at 10° C./min above this temperature, followed by a period of 15 min at the final temperature of 1,500° C., followed by a cooling cycle symmetrical to the heating cycle.

In practise the required softening begins to occur at around 1,300° C, and is virtually complete at 1,450° C.

In practise this softening leads to flattening of the cylindrical ring 29 along its shorter axis by around 10%, the flattening being more accentuated in the areas in contact with the load than in the areas remote from the latter.

In the embodiment shown (FIG. 5C) the load C is applied along one generatrix of the cylindrical ring 29 with the resisting load C' along its opposite generatrix.

As an alternative to this, however, it may be divided between a number of generatrices of the cylindrical ring 29, with a symmetrical distribution of the resisting load.

Be this as it may, when it softens, the initially cylindrical ring 29 is formed into a flattened ring 27 whose contour is generally elliptical.

The flattened ring 27 is further shaped according to the final shape required for the ceramic facings 22 before it is cut.

According to the invention, this is achieved by expanding it.

To be more precise, the flattened ring 27 is placed in a mold 32 made from refractory material whose coefficient of thermal expansion is less than its own and the combination is raised to a temperature such that, given the two coefficients of thermal expansion and the initial peripheral clearance J between the flattened ring 27 and the mold 32, the flattened ring 27 is pressed against the mold 32.

In the case of a flattened ring 27 made from zirconia, for example, whose coefficient of expansion is in the order of $1.7 \times 10^{-5}/°C$ the mold 32 is made from alumina whose coefficient of expansion is in the order of $0.7 \times 10^{-5}/°C$.

The flattened ring 27 is placed cold into the mold 32 and the combination is then heated to 1,500° C.

At this temperature the linear shrinkage of the zirconia is approximately 1 mm greater than that of the alumina for an overall size of 60 mm.

The differential expansion presses the flattened ring 27 perfectly against the mold 32 so that it assumes the shape of the mold 32, as shown in FIG. 5E.

The shaped flattened ring 27 is removed after cooling and cut.

The facing blanks 22' obtained by this process can have a thickness in the order of 1 to 2 mm, for example.

Of course, the various numerical values given above are given by way of example only and must not be regarded as in any way limiting the invention.

The resulting facing blanks 22' are then machined, in particular to taper them at the front.

The ceramic facings 22 are polished, of course.

They can be polished before or after they are fitted to the lateral branches 16 of the femoral part 15.

Be this as it may, they are polished using a conventional technique such as diamond paste polishing, for example.

As shown in FIGS. 6A and 6B, another method in accordance with the invention for producing a facing blank 22' is to force a ceramic plate 33 at high temperature into a groove 34 shaped to the required profile of the facing blank 22'.

The groove 34 is in practise machined into a refractory material shaping member 35.

As shown in FIG. 6A, the ceramic plate 33 is obtained, for example, by cutting an initially parallelepiped-shaped ceramic block 36.

Be this as it may, the facing blanks 22' obtained are subsequently processed as described above.

A third method in accordance with the invention for producing a facing blank 22' uses hot forming under load, exploiting the plastic flow property of the ceramic when heated above a particular temperature.

Experience shows and experiments confirm that it is a very simple matter to produce the required facing blank 22' reproducibly.

To be more precise, the third method in accordance with the invention uses a mold 40 (FIGS. 7 to 9).

The mold is in two parts 40A and 40B.

In the embodiment shown here, the two parts 40A and 40B are disposed one above the other and the lower part 40B carries guides 42 on which the upper part 40A slides by means of bores 43 formed in it.

For example, when the combination is a generally parallelepiped-shape block, as shown, guides 42 may be provided along each of the longer edges of the block.

The embodiment shown is a test prototype with three guides 42 provided along each edge in the form of circular cross-section rods.

Of course, their number can be reduced and/or their layout can be changed.

To define the required molding cavity either part 40A or 40B of the mold 40, the part 40B in this embodiment, has in the median part of a shoulder 44 a recess 45 whose overall contour is that of the required ceramic facing 22.

The other part of the mold 40, that is the part 40A in this embodiment, has in the median part of a shoulder 46 a projecting boss 47 of complementary shape to the recess 45 and adapted to be inserted into the latter.

In this embodiment the recess 45 in the part 40B and the boss 47 on the part 40A are defined by parallel generatrices, in the manner of cylindrical walls, and extend transversely over the full width of the parts 40A and 40B.

In practise the shoulders 44 and 46 in the median areas of which said recess 45 and said boss 47 are provided are generally perpendicular to the guides 42.

As shown in FIG. 7, a taper d is preferably provided between the lateral surfaces of the recess 45 and the boss 47, for reasons that will be explained later.

As shown in FIGS. 8 and 9, the part 40B in which the recess 45 is formed preferably has a recess 48 in its median part between the guides 42 and extending transversely along the full length of the recess 45, also for reasons that will be explained later.

In practise this recess has a flat bottom and perpendicular sides and is relatively shallow.

Note that the recess 48 does not extend onto the shoulder 44.

In practise the two parts 40A and 40B of the mold 40 are made from graphite.

The guides 42 may be made from molybdenum, for example.

The manufacture in accordance with the invention of a ceramic facing 22 to be fitted to the femoral part 15 entails first obtaining a facing blank 22' by inserting a ceramic plate 33 between the two parts 40A and 40B of the mold 40 and bringing the latter together at high temperature.

As previously mentioned, the ceramic plate 33 can be obtained by cutting a ceramic block, for example a zirconia block.

In this embodiment its contour is rectangular.

Its length L1 is chosen to be equal to the developed length of the facing blank 22'.

Its width L2 is chosen to be greater than the width L3 of the recess 48 in the part 40B of the mold 40 but less than the distance between the two rows of guides 42 on the latter.

Initially the ceramic plate 33 is simply placed on the shoulder 44 of the part 40B of the mold 40 (FIG. 11A).

It therefore extends across the recess 45 in the part 40B, between the guides 42.

Positioned on the guides 42, the part 40B of the mold 40 rests due to its own weight on the ceramic plate 33.

The combination is then placed in an evacuated furnace whose temperature is gradually increased to 1,500° C.

The two parts 40A and 40B of the mold 40 are then moved gradually together, preferably under load.

In this embodiment the two parts 40A and 40B being disposed one above the other, the part 40A applies the necessary load by virtue of its own weight.

An additional weight 50 may be used if required, as schematically represented in chain-dotted outline in FIGS. 11A, 11B and 11C.

Be this as it may, as they move towards each other the two parts 40A and 40B of the mold 40 are advantageously guided relative to each other by the guides 42.

At 1,300° C., and as shown in FIG. 11B, the ceramic plate 33 is softened by plastic flow and due to the load applied by the part 40A of the mold 40 it gradually bends until it matches the shape of the recess 45 in the part 40B on completion of the movement towards the latter of the part 40A (FIG. 11C).

The temperature is then maintained at this value for a predetermined time, for ten minutes, for example.

As zirconia has a coefficient of thermal expansion greater than that of graphite, the facing blank 22' may tend during subsequent cooling to shrink onto the boss 47 on the part 40A of the mold 40, with the risk of it breaking.

As will be readily understood, the purpose of the taper d between the boss 47 and the recess 45 is to prevent any such consequences by providing the ceramic plate 33 with the necessary clearance.

The taper d may be approximately 0.2 mm, for example.

The recess 48 in the median part of the recess 45 in the part 40B of the mold 40 advantageously avoids edge effects causing transverse bending of the ceramic plate 33 in addition to the required longitudinal bending.

As the zirconia from which the initial ceramic plate 33 is made is shaped at high temperature in a vacuum and in the presence of the graphite from which the two parts 40A and 40B of the mold 40 are made, the zirconia is inevitably blackened.

All that is required to remove this blackening is to reheat the facing blank 22' to 1,500° C. in pure air.

As already mentioned, the method of manufacturing the ceramic facing 22 then entails machining and polishing the facing blank 22'.

As shown in chain-dotted outline in FIG. 12, the developed length of the facing blank 22' may be sufficient for the latter to be snap-fastened to the corresponding lateral branch 16 of the femoral part 15.

Likewise, according to a further feature of the invention, and as shown in FIG. 13, the mold 40 employed may be adapted to enable the simultaneous forming in one piece of a facing blank 22" comprising two branches 22' each corresponding to a respective lateral branch 16 of the femoral part 15 and, between them at their root, a groove 53 corresponding to the groove 21 on the femoral part 15.

At least part of the groove 21 is therefore also provided with a ceramic facing.

The same applies to the embodiment shown in FIG. 14, in which a ceramic facing 52 separate from the ceramic facings 22 is applied to the groove 21.

Of course, the present invention is not limited to the embodiments described and shown but encompasses any variant execution and/or combination of their various component parts.

In particular, in the case of manufacture by shaping, all or part of the necessary shaping force can be applied by a piston-and-cylinder actuator.

All the methods used to manufacture a preformed ceramic facing to be fitted to the femoral part have the common feature of starting from a pre-existing ceramic part whose shape is different from the required final shape and shaping it, in practise at high temperature, to adapt it to the femoral part to which it is to be fitted.

It should further be emphasized that, by extension, the word "ceramic" used herein for convenience must be understood as meaning not only ceramics proper but also, and more generally, all materials, and in particular composite materials, such as for example carbon/carbon materials and carbon/silicon materials, having comparable characteristics, and in particular hardness characteristics, composite materials in particular lending themselves to the necessary polishing after application to them of an appropriate coating, of pyrolitic carbon, for example, even if they are not in themselves initially adapted to be polished.

Finally, the field of application of the invention is not limited to the case where, as specifically described and shown, the femoral part is fork-shaped.

To the contrary, it also encompasses the case of a single-compartment prosthesis in which the femoral part has only one branch.

I claim:

1. A femoral part of a knee prosthesis comprising a metal support member having an internal surface adapted to be secured to a femur, and an external surface adapted to roll and slide on an associated tibial part of the knee prosthesis, a solid ceramic liner strip being fixed to the external surface of the support member and defining a contact surface for engagement with a complementary portion of the tibial part.

2. A femoral part of a knee prosthesis comprising a metal support member having an internal surface adapted to be secured to a femur, and an external surface adapted to face an associated tibial part of the knee prosthesis, a solid ceramic liner strip being fixed to the external surface of the support member defining a contact surface for engagement with a complementary portion of the tibial part, said support member having a generally curved fork shape including two lateral branches joined together by a median part, the inner surface of each of the lateral branches being adapted to be applied to a respective condyle of the femur and the outer surface of the lateral branches being associated with glenes of the associated component, a said liner strip being fixed to the outer surface of each of said lateral branches.

3. A femoral part according to claim 2, wherein each of said ceramic liner strips is made of zirconia.

4. A femoral part according to claim 3, wherein each of said liner strips extends along the entire operative portion of the outer surfaces of the respective lateral branches.

5. A femoral part according to claim 2, wherein the width of the strips generally tapers from the rear towards the front.

6. A femoral part according to claim 2, further comprising means crimping said liner strips to said support member.

7. A femoral part according to claim 2, further comprising an adhesive bonding means fixing said liner strips to said support member.

8. A femoral part according to claim 1, wherein damping means are disposed between each of said liner strips and the support member.

9. A femoral part according to claim 8, wherein a groove is defined in said median part to form a trochlea, and a solid ceramic liner strip at least partially overlying an outer surface of the median part.

* * * * *